United States Patent
Drubin et al.

(10) Patent No.: US 6,300,084 B1
(45) Date of Patent: Oct. 9, 2001

(54) ANTI-MITOTIC AGENT SCREENING PROCESS

(75) Inventors: David G. Drubin, Berkeley, CA (US); Christian J. Hofmann, Munich (DE)

(73) Assignee: The Regents of the University of California, Berkeley, CA (US)

( * ) Notice: Subject to any disclaimer, the term of this patent is extended or adjusted under 35 U.S.C. 154(b) by 0 days.

(21) Appl. No.: 09/414,828

(22) Filed: Oct. 6, 1999

Related U.S. Application Data

(60) Provisional application No. 60/103,684, filed on Oct. 8, 1998.

(51) Int. Cl.[7] ............................. G01N 33/53; C07K 1/00; C07K 14/00; C07K 17/00; C07H 21/02
(52) U.S. Cl. ..................... 435/7.1; 530/350; 536/23.1; 435/320; 435/325; 435/477; 514/44; 424/93.21; 424/277.1
(58) Field of Search ....................... 435/320, 325, 435/477, 7.1; 424/277.1, 93.21; 514/44; 536/23.1; 530/356, 350

(56) References Cited

PUBLICATIONS

J. M. Nigro et al., Molecular and Cellular Biology, "Human p53 and CDC2Hs Genes Combine To Inhibit the Proliferation of *Saccharomyces cerevisiae*," Mar. 1992, vol. 12, No. 3, pp. 1357–1365.*
W. French Anderson. Human gene therapy. Nature, vol. 392, pp. 25–30, 1998.*
T. Gura. Systems for identifying new drugs are often faulty. Science, vol. 278, pp. 1041–1042, 1997.*
Hartwell et al. Integrating genetic approaches into the discovery of anti–cancer drugs. Science, vol. 278, pp. 1064–1067, 1997.*
Hofmann, Christian, et al, "*Saccharomyces cerevisiae* Duo 1p and Dam 1p, Novel Proteins Involved in Mitotic Spindle Function", Nov. 16, 1998, Department of Molecular and Cell Biology, University of California, Berkeley, The Journal of Cell Biology, vol. 143, No. 4, pp. 1029–1040.
Jones, Michele H., et al., "Yeast Dam1p Is Required to Maintain Spindle Integrity during Mitosis and Interacts with the Mps1p Kinase", Jul. 1999, Department of Molecular, Cellular, and Developmental Biology, University of Colorado, vol. 10, pp. 2377–2391.
Search SGD, http://genome–www.standford.edu/saccharomyces/.
Cheesman, Iain M., "DUO1p and DAM1p, Two Novel Proteins Important for Mitotic Spindle Function in *Saccharomyces Cerevisiae*" Abstracts, Nov. 1998, Supplement to Molecular Biology of the Cell, vol. 9, p. 248.
Pasqualone, Danielle, et al., "STU1, a Suppressor of a B–Tubulin Mutation, Encodes a Novel and Essential Component of the Yeast Mitotic Spindle", Dec. 1994, Section of Biochemistry, Molecular and Cell Biology, Cornell University, vol. 127, No. 6, Part 2, pp. 1973–1984.
Feuermann, M., et al., "The Characterization of Two New Clusters of Duplicated Genes Suggests a [Lego] Organization of the Yeast *Saccharomyces cerevisiae* Chromosomes", 1997, Yeast Sequencing Reports, vol. 13, pp. 861–869.
Hoyt, Andrew, M., et al., "Genetic Analysis of the Mitotic Spindle", 1996, Department of Biology, The Johns Hopkins University, pp. 7–33.
Hansen, et al., "the Sequence of a 23•4 kb Segment on the Right Arm of Chromosome VIII From *Saccharomyces cerevisiae*Reveals CLB6, SPT6, RP28A and NUP57 Genes, a Ty3 Element and 11 New Open Reading Frames", Yeast Sequencing Reports, Received Feb. 15, 1996, accepted May 26, 1996, vol. 12, pp. 1273–1277.

* cited by examiner

*Primary Examiner*—Jill D. Martin
*Assistant Examiner*—Peter Paras, Jr.
(74) *Attorney, Agent, or Firm*—Beyer Weaver & Thomas, LLP

(57) ABSTRACT

Provided is a genetic identification and characterization of a gene which encodes an essential yeast mitotic spindle protein. The protein functions in anaphase spindle elongation. The invention also provides an identification of a protein which interacts with this mitotic spindle protein. The proteins identified and characterized by the present invention are useful as development candidates for cancer chemotherapeutic agents, anti-fungal compounds, and other antimitotic agents.

9 Claims, 4 Drawing Sheets

Table 1. Strains used

| Name | Mat | Genotype |
| --- | --- | --- |
| DDY757 | a | *cry1, ade2-1, his3-11,15, leu2-3,112, ura3-1, trp1-1, can1-100* |
| DDY759 | a/α | *cry1/cry1, ade2-1/ade2-1, his3-11,15/his3-11,15, leu2-3,112/leu2-3,112, ura3-1/ura3-1 trp1-1/trp1-1, can1-100/can1-100* |
| DDY898 | a | *his3Δ200, ura3-52* |
| DDY1102 | a/α | *ade2-1/+, his3Δ200/his3Δ200, leu2-3,112,/leu2-3,112 ura3-52/ura3-52, lys2-801/+* |
| DDY1445 | a/α | *his3Δ200/his3Δ200, leu2-3,112/leu2-3,112, ura3-52/ura3-52, ade2-1/+* |
| DDY1446 | a/α | *his3Δ200/his3Δ200, leu2-3,112/leu2-3,112, ura3-52/ura3-52, ade2-1/+ Δduo1:HIS3/ Δduo1:HIS3 pDD476* |
| DDY1447 | a/α | *his3Δ200/his3Δ200, leu2-3,112/leu2-3,112, ura3-52/ura3-52, ade2-1/+ Δduo1:HIS53/ Δduo1:HIS3, pDD477* |

FIG. 2

| Strain | Time after temperature shift (hrs) | ⬭ | ⬭⬭ | ⬭■⬭ | ⬭⬭ | ⬭⬭ | No microtubule structures |
|---|---|---|---|---|---|---|---|
| wild type | 0 | 31 | 35 | 34 | | | |
| | 3 | 30 | 37 | 33 | | | |
| | 6 | 28 | 40 | 32 | | | |
| | 9 | 31 | 39 | 30 | | | |
| | 12 | 36 | 37 | 27 | | | |
| duo1-1 | 0 | 24 | 31 | 31 | 14 | | |
| | 3 | 20 | 18 | 21 | 41 | | |
| | 6 | 21 | 10 | 14 | 55 | | |
| | 9 | 17 | 8 | 8 | 62 | 5 | 2 |
| | 12 | 11 | 2 | 4 | 65 | 9 | 9 |
| duo1-2 | 0 | 25 | 27 | 31 | 13 | 4 | |
| | 3 | 25 | 5 | 10 | 57 | 3 | 3 |
| | 6 | 21 | 5 | 8 | 58 | 5 | |
| | 9 | 14 | 2 | 4 | 43 | 3 | 35 |
| | 12 | 13 | 2 | 1 | 30 | 3 | 52 |

TABLE 2

FIG. 3

SEQUENCE LISTING

<160> NUMBER OF SEQ ID NOS: 15

<210> SEQ ID NO 1
<211> LENGTH: 24
<212> TYPE: DNA
<213> ORGANISM: Saccharomyces cerevisiae

<400> SEQUENCE: 1
ccatcgatat tgaagacttg ttca                                          24

<210> SEQ ID NO 2
<211> LENGTH: 27
<212> TYPE: DNA
<213> ORGANISM: Saccharomyces cerevisiae

<400> SEQUENCE: 2
ggactagtga gcaaagccaa ttagatg                                       27

<210> SEQ ID NO 3
<211> LENGTH: 32
<212> TYPE: DNA
<213> ORGANISM: Saccharomyces cerevisiae

<400> SEQUENCE: 3
gcgcgtctag acccgaatct taattattta cc                                 32

<210> SEQ ID NO 4
<211> LENGTH: 33
<212> TYPE: DNA
<213> ORGANISM: Saccharomyces cerevisiae

<400> SEQUENCE: 4
gcgcccatgg agcaaagcca ataagatgat tcg                                33

<210> SEQ ID NO 5
<211> LENGTH: 22
<212> TYPE: DNA
<213> ORGANISM: Saccharomyces cerevisiae

<400> SEQUENCE: 5
gcggatccta gatacattcc cg                                            22

<210> SEQ ID NO 6
<211> LENGTH: 20
<212> TYPE: DNA
<213> ORGANISM: Saccharomyces cerevisiae

<400> SEQUENCE: 6
gagatctgga attcggatcc                                               20

<210> SEQ ID NO 7
<211> LENGTH: 21
<212> TYPE: DNA

-continued

<213> ORGANISM: Saccharomyces cerevisiae

<400> SEQUENCE: 7
ggcatgccgg tagaggtgtg g                                             21

<210> SEQ ID NO 8
<211> LENGTH: 36
<212> TYPE: DNA
<213> ORGANISM: Saccharomyces cerevisiae

<400> SEQUENCE: 8
gcgggatcca tgagcgaaga taaagctaaa ttaggg                             36

<210> SEQ ID NO 9
<211> LENGTH: 25
<212> TYPE: DNA
<213> ORGANISM: Saccharomyces cerevisiae

<400> SEQUENCE: 9
ctagtctaga atcagtcagc tcatc                                         25

<210> SEQ ID NO 10
<211> LENGTH: 82
<212> TYPE: DNA
<213> ORGANISM: Saccharomyces cerevisiae

<400> SEQUENCE: 10
ctgataagct cagcaattgc accaaaacaa tatgagaaaa ggcttgtatt gccactttca   60
ccgattgtac tgagagtgca cc                                            82

<210> SEQ ID NO 11
<211> LENGTH: 81
<212> TYPE: DNA
<213> ORGANISM: Saccharomyces cerevisiae

<400> SEQUENCE: 11
ttgtgaggag gataattctt tggttgggtt gggcgtagtc atctgaaggg gggccttgta   60
ctgtgcggta tttcacaccg a                                             81

<210> SEQ ID NO 12
<211> LENGTH: 20
<212> TYPE: DNA
<213> ORGANISM: Saccharomyces cerevisiae

<400> SEQUENCE: 12
gcgttgcccg gacaatatcg                                               20

<210> SEQ ID NO 13
<211> LENGTH: 19
<212> TYPE: DNA
<213> ORGANISM: Saccharomyces cerevisiae

<400> SEQUENCE: 13
ctgccttcct ccctattgc                                                19

<210> SEQ ID NO 14
<211> LENGTH: 247
<212> TYPE: PRT
<213> ORGANISM: Saccharomyces cerevisiae

<400> SEQUENCE: 14

Met Ser Glu Gln Ser Gln Leu Asp Asp Ser Thr Ile Asp Lys Leu Ile

```
                1               5                      10                     15
        Pro Gln Ile Phe Asn Glu Met Arg Ser Asn Leu Asn Asn Thr Thr Asn
                            20                  25                  30
        Lys Phe Pro Lys Ser Thr Gly Gly Ala Ser Asp Asn Ile Ser Ala
                    35                  40                  45
        Asn Ser Asn Ser Ile Arg Ser Phe Asn Ser Ile Thr Thr Gln Ser Leu
                50                  55                  60
        Leu Lys Glu Ser Glu Ser Leu Asp Lys Ile Thr Ala Met Ile Lys Asn
        65                  70                  75                  80
        Val Thr Ala Ala Leu Lys Asn Asn Leu Pro Val Tyr Val Asn Gln Val
                        85                  90                  95
        His Glu Val Cys Lys Ser Thr Asn Ser Ile Leu Asp Ser Trp Ile Asn
                    100                 105                 110
        Ile His Ser Gln Ala Gly Tyr Ile His Lys Leu Met Ser Asp Gln Thr
                    115                 120                 125
        Tyr Leu Lys Leu Ile Asn Asp Arg Leu His Asn Glu Asn Val Asn Thr
                    130                 135                 140
        Asn Asp Glu Asp Gly Ser Thr Leu His Asn Val Ile Ala Leu Lys Lys
        145                 150                 155                 160
        Lys Glu Ile Leu Asp Leu Arg Gln Lys Leu Glu Asn Arg Lys Gly Glu
                        165                 170                 175
        Lys Asp Ala Ala Pro Ala Lys Pro Pro Asn Gln Gly Leu Asn Pro Arg
                    180                 185                 190
        Tyr Gly Val Gln Ser Gly Arg Arg Pro Val Pro Ser Ala Gly Ile Ser
                    195                 200                 205
        Asn Asn Gly Arg Val Arg Lys Thr His Val Pro Ala Ser Lys Arg Pro
            210                 215                 220
        Ser Gly Ile Pro Arg Val Thr Asn Arg Trp Thr Lys Pro Thr Ala Ser
        225                 230                 235                 240
        Ser Ser Arg Lys Met Phe Arg
                        245

<210> SEQ ID NO 15
<211> LENGTH: 335
<212> TYPE: PRT
<213> ORGANISM: Saccharomyces cerevisiae

<400> SEQUENCE: 15

Met Ser Glu Asp Lys Ala Lys Leu Gly Thr Thr Arg Ser Ala Thr Glu
        1               5                   10                  15
        Tyr Arg Leu Ser Ile Gly Ser Ala Pro Thr Ser Arg Arg Ser Ser Met
                    20                  25                  30
        Gly Glu Ser Ser Ser Leu Met Lys Phe Ala Asp Gln Glu Gly Leu Thr
                    35                  40                  45
        Ser Ser Val Gly Glu Tyr Asn Glu Asn Thr Ile Gln Gln Leu Leu Leu
                50                  55                  60
        Pro Lys Ile Arg Glu Leu Ser Asp Ser Ile Thr Leu Asp Ser Asn
        65                  70                  75                  80
        Phe Thr Arg Leu Asn Phe Ile His Glu Ser Leu Ala Asp Leu Asn Glu
                        85                  90                  95
        Ser Leu Gly Ser Leu Leu Tyr Gly Ile Met Ser Asn Ser Trp Cys Val
                    100                 105                 110
        Glu Phe Ser Gln Ala Pro His Asp Ile Gln Asp Asp Leu Ile Ala Ile
                    115                 120                 125
```

-continued

```
Lys Gln Leu Lys Ser Leu Glu Asp Glu Lys Asn Asn Leu Val Met Glu
        130             135             140

Leu Ser Asn Met Glu Arg Gly Ile Lys Arg Lys Lys Asp Glu Gln Gly
145             150             155             160

Glu Asn Asp Leu Ala Lys Ala Ser Gln Asn Lys Gln Phe Asn Gln Pro
                165             170             175

Leu Phe Pro Ser Ser Gln Val Arg Lys Tyr Arg Ser Tyr Asp Asn Arg
            180             185             190

Asp Lys Arg Lys Pro Ser Lys Ile Gly Asn Asn Leu Gln Val Glu Asn
        195             200             205

Glu Glu Asp Tyr Glu Asp Asp Thr Ser Ser Glu Ala Ser Phe Val Leu
        210             215             220

Asn Pro Thr Asn Ile Gly Met Ser Lys Ser Ser Gln Gly His Val Thr
225             230             235             240

Lys Thr Thr Arg Leu Asn Asn Asn Thr Asn Ser Lys Leu Arg Arg Lys
                245             250             255

Ser Ile Leu His Thr Ile Arg Asn Ser Ile Ala Ser Gly Ala Asp Leu
                260             265             270

Pro Ile Glu Asn Asp Asn Val Val Asn Leu Gly Asp Leu His Pro Asn
        275             280             285

Asn Arg Ile Tyr Ser Glu Val Val Leu Gln Glu Trp Ser Met Gly Pro
        290             295             300

Leu Arg Arg Thr Glu Ile Gln Cys Ser Gln Asp Val Leu Lys Gly Asn
305             310             315             320

Pro Gln Lys Ala Asp Ile Leu Leu Gln Arg Lys Leu Lys Lys Lys
                325             330             335
```

ANTI-MITOTIC AGENT SCREENING PROCESS

CROSS-REFERENCE TO RELATED APPLICATIONS

This application claims priority to United States Provisional Patent Application Ser. No. 60/103,684 entitled MITOTIC SPINDLE PROTEINS, filed Oct. 8, 1998, the disclosure of which is incorporated by reference herein for all purposes.

This invention was made with Government support under Grant No. GM-50399 awarded by the National Institute of General Medical Sciences of the National Institutes of Health. The Government has certain rights to this invention.

BACKGROUND OF THE INVENTION

This invention relates generally to the identification and characterization of fungal genes and proteins, and in particular to mitotic spindle proteins useful as development candidates for anti-mitotic agents and processes using such agents.

The mitotic spindle undergoes a remarkable series of transitions in response to cell cycle control signals. At each mitotic cell division, the spindle assembles, it forms attachments to each chromosome, it orients itself properly within the cell, and then, with extraordinarily high fidelity, it carries out chromosome segregation. Then it disassembles.

Proper spindle assembly and function involves coordination of many events and processes including modulation of microtubule dynamics and creation of at least three distinct microtubule populations (kinetochore, polar, and astral microtubules). In addition, connections must be established between different spindle microtubule subpopulations, between spindle microtubules and chromosomes, between spindle microtubules and microtubule-associated proteins and motor proteins, and between spindle microtubules and the cell cortex (reviewed by Waters and Salmon, 1997). Proper spindle assembly is monitored by a cellular surveillance system which activates a mitotic checkpoint if the spindle is not assembled correctly (reviewed by Hardwick, 1998; Rudner and Murray, 1996). Once the spindle is assembled, a carefully orchestrated set of molecular events results in chromosome to pole movement (anaphase A) and separation of spindle poles (anaphase B).

Genetic approaches to the study of spindle mechanics and regulation in S. cerevisiae, S. pombe, A. nidulans, and in a variety of other organisms have complemented studies in Xenopus extracts and mammalian and plant cells (reviewed by Nicklas, 1997; Sobel, 1997). Each different approach has provided an extremely powerful and unique avenue toward identification of mitotic spindle components and elucidation of their functions. Budding yeast contains five kinesin-related motor proteins and one dynein (reviewed by Winsor and Schiebel, 1997). Elegant genetic studies in yeast have revealed how the forces generated by these proteins work both synergistically and antagonistically to assemble and orient spindles, and to separate chromosomes (Cottingham and Hoyt, 1997; Gambino et al., 1984; Oakley and Morris, 1980; Oakley and Rinehart, 1985; Saunders and Hoyt, 1992).

It is believed that a large number of proteins in the spindle function in concert with tubulin, the major spindle protein. Genetic studies have identified and provided functional tests of γ-tubulin and many other proteins associated with spindle pole bodies (Marschall et al., 1996; Oakley, 1994; Rout and Kilmartin, 1990; Sobel and Snyder, 1995; Spang et al., 1995). Also, a number of spindle accessory proteins have been found and studied functionally (Berlin et al., 1990; Machin et al., 1995; Pasqualone and Huffaker, 1994; Pellman et al., 1995; Wang and Huffaker, 1997). These genetic studies have been particularly valuable both because non-tubulin spindle components are typically low in abundance, making their discovery difficult by other means, and because genetic analysis facilitates tests of function in vivo.

As indicated above, the mitotic spindle has been the subject of considerable research. The study of mitotic spindle proteins has yielded anti-mitotic compounds with important applications in cancer chemotherapy, and therapeutic agents targeted against fungal pathogens. For example, several plant and fungal secondary metabolites such as colchicine, vinblastine and taxol have been shown to interfere with mitotic spindle function in a wide variety of eukaryotes.

The demonstrated effectiveness of these anti-mitotic compounds in important medical and agricultural applications demonstrates the desirability of identifying and characterizing anti-mitotic compound development candidates.

SUMMARY OF THE INVENTION

To achieve the foregoing, the present invention provides a genetic identification and characterization of a gene which encodes an essential yeast mitotic spindle protein. The protein functions in proper spindle assembly and anaphase spindle elongation. The invention also provides an identification of a protein which interacts with this mitotic spindle protein. The proteins identified and characterized by the present invention are useful as development candidates for cancer chemotherapeutic agents, anti-fungal compounds, and other anti-mitotic agents.

In one aspect, the present invention provides a nucleic acid vector including a gene which encodes an essential mitotic spindle protein, and a plasmid capable of incorporating that gene. In preferred embodiments, the gene is the yeast gene YGL061c or the yeast gene YGR113w, and the plasmid is Bluescrpit SK$^+$ vector (pDD478).

In another aspect, the invention provides a substantially pure protein essential to mitotic spindle formation. In preferred embodiments, the protein includes an amino acid sequence coded for by the yeast gene YGL061c or the yeast gene YGR113w.

In still another aspect, the present invention provides a binding protein for a protein essential to mitotic spindle formation. The binding protein includes an amino acid sequence coded for by the yeast gene YGR113w.

In yet another aspect, the present invention provides a composition useful as a development candidate for an anti-mitotic agent. The development candidate includes an amino acid sequence selected from at least one of an amino acid sequence coded for by the yeast gene YGL061c, and an amino acid sequence coded for by the yeast gene YGR113w.

In an additional aspect, the invention also provides an anti-mitotic agent identified by a screening method using one or more proteins essential to mitotic spindle formation. In preferred embodiments, the one or more proteins include an amino acid sequence selected from at least one of an amino acid sequence coded for by the yeast gene YGL061c, and an amino acid sequence coded for by the yeast gene YGR113w.

In a further aspect, the invention provides a method of disrupting mitotic spindle formation in a cell. The method involves administering to the cell an anti-mitotic agent that disrupts the activity of one or more proteins essential to mitotic spindle formation. The one or more proteins include an amino acid sequence selected from at least one of the amino acid sequence coded for by the yeast gene YGL061c, and the amino acid sequence coded for by the yeast gene YGR113w.

These and other features and advantages of the present invention will be presented in more detail in the following description of the invention and the accompanying figures which illustrate by way of example the principles of the invention.

BRIEF DESCRIPTION OF THE DRAWINGS

FIG. 2 shows the yeast strains used in the identification and characterization of genes and proteins in accordance with the present invention, listed in Table 1.

FIG. 3 shows the results of experiments undertaken to examine the temperature-sensitivity of the phenotype of a gene coding for an essential mitotic spindle protein in accordance with the present invention, noted in Table 2.

DETAILED DESCRIPTION OF PREFERRED EMBODIMENTS

Figure 1A:
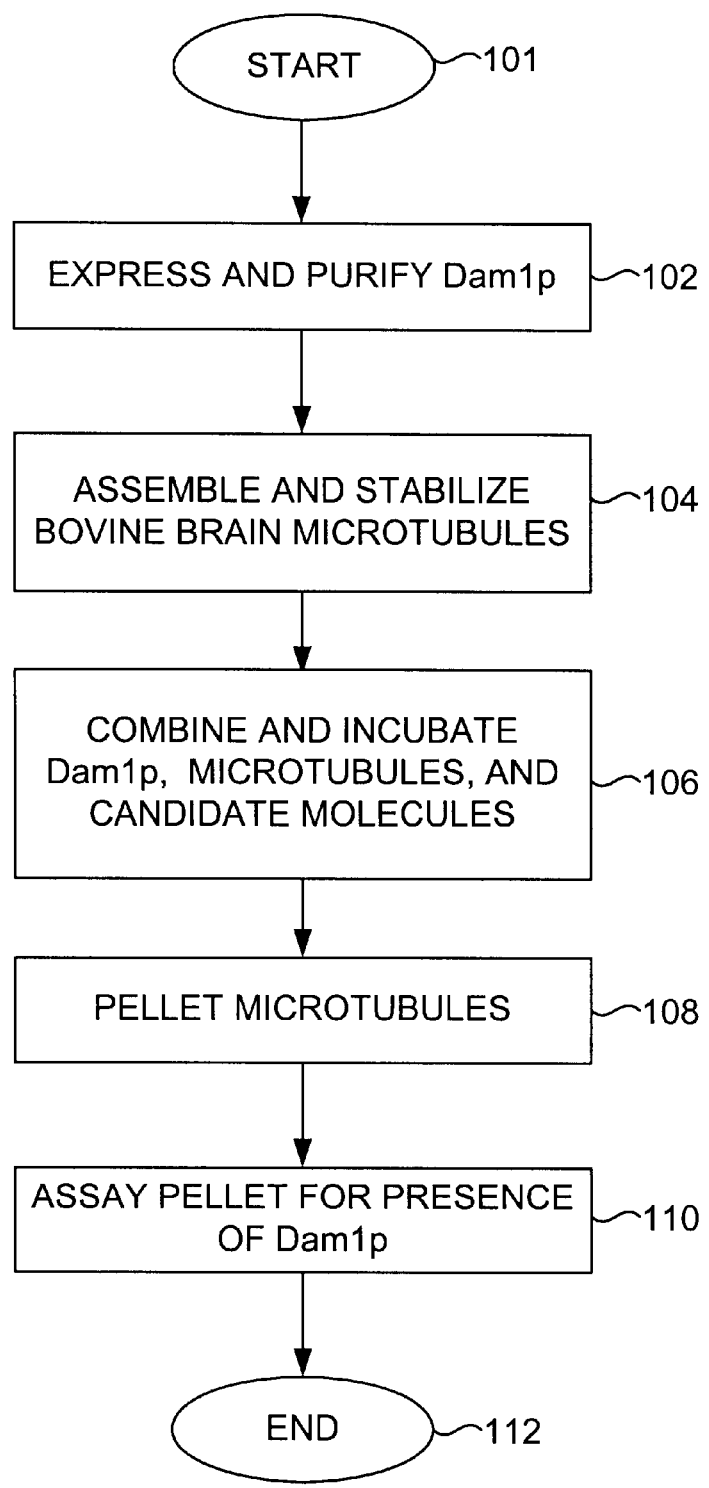
FIGS. 1A and 1B depict process flow diagrams illustrating anti-mitotic agent screening protocols using proteins in accordance with preferred embodiments of the present invention.

The present invention will now be described with reference to preferred embodiments. Important properties and characteristics of the preferred embodiments are described in the text and illustrated in the accompanying drawings. While the invention will be described in conjunction with these preferred embodiments, it should be understood that the invention is not intended to be limited to these preferred embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

The present invention provides a genetic identification and characterization of a gene which encodes an essential yeast mitotic spindle protein. The protein functions in proper spindle assembly and anaphase spindle elongation. The invention also provides an identification of a protein which interacts with this mitotic spindle protein. The proteins identified and characterized by the present invention are useful as development candidates for cancer chemotherapeutic agents, anti-fungal compounds, and other anti-mitotic agents.

The identification and characterization of the two novel and essential mitotic spindle proteins according to one aspect of the present invention, Duo1p and Dam1p, is described below. Duo1p was isolated because its overexpression caused defects in mitosis and a mitotic arrest. Duo1p was localized by immunofluorescence, by immunoelectron microscopy, and by tagging with green fluorescent protein (GFP), to intranuclear spindle microtubules and spindle pole bodies (SPBs). Temperature-sensitive duo1 mutants showed defects in proper spindle assembly and elongation. Dam1p was identified by two-hybrid analysis as a protein which binds to Duo1p. No homologues of Duo1p or Dam1p were identified in the sequence databases. By expressing a GFP-Dam1p fusion protein in yeast, Dam1p was shown to be associated with intranuclear spindle microtubules in vivo. Overproduction of Dam1p caused mitotic defects similar to those caused by Duo1p overproduction. Biochemical experiments demonstrated that Dam1p is a microtubule-binding protein. It is believed that Dam1p localizes Duo1p to intranuclear microtubules to provide a previously unrecognized function (or functions) required for proper spindle assembly and elongation.

Both Duo1p and Dam1p proteins are promising as anti-mitotic compound development candidates. Knowing that these proteins are each essential to proper mitotic cell division, screening studies may be performed using these proteins as targets in order to identify compounds which bind to the proteins and prevent them from carrying-out their intended functions. Such compounds would then have anti-mitotic activity and may be useful in a variety of applications.

For example, since cancer cells undergo mitotic division at a faster rate than normal cells, an anti-mitotic compound identified by screening studies using the proteins of the present invention may be useful as a cancer chemotherapeutic agent. The anti-mitotic action of the agent would have a disproportionately greater effect on rapidly dividing cancer cells than on normal cells.

In addition, fungal infections are a common affliction of both humans and animals, and agricultural crops and products. Anti-mitotic agents developed using the proteins of the present invention may be useful as drugs and pesticides to prevent or treat such fungal infections. Application of these proteins to the development of anti-fungal agents for use as pesticides on agricultural crops and for pharmaceutical applications may be particularly useful, since the lack of homology (with mammalian and, particularly, human sequences known to date) between these proteins and human proteins suggests that anti-mitotic agents effective against these fungal proteins would not have anti-mitotic activity against human cells thereby preventing any adverse health effects for humans contacting these agents.

A variety of screening procedures may be used to identify anti-mitotic compounds using proteins in accordance with the present invention. Such screening procedures may exploit either of the two molecular interactions which have been established: the binding of Dam1p directly to microtubules, polymers of the protein tubulin; and the binding of Dam1p and Duo1p directly to each other. Moreover, screening protocols focussing on gene expression may also be used, as discussed below.

One preferred screening procedure using the Dam1p-microtubule interaction is illustrated in the process flow of FIG. 1A. The process begins at a step 101, and at a step 102, Dam1p is expressed and purified, preferably to 90% or greater purity, using a bacterial or yeast expression system. At a step 104, bovine brain microtubules are assembled under standard conditions, then stabilized with taxol. Molecules that are candidates for the inhibition of the Dam1p-microtubule interaction by binding to Dam1p are then screened for as follows: The Dam1p, microtubules, for example about 10 $\mu$M, and candidate molecules (for example, small organic molecules having a molecular weight of from about 300 to 800 Daltons, or peptides) are combined and incubated, at a step 106. Then, at a step 108, a low-throughput procedure is used to pellet microtubules by ultracentrifugation. The pellet is then assayed by polyacrylamide gel electrophoresis for presence of Dam1p at a step 110. Absence of Dam1p in the microtubule pellet indicates that the candidate molecule inhibits the Dam1p-microtubule interaction and is therefore a promising anti-mitotic agent development candidate. The process ends at 112.

For high-throughput assays, a fluorescent probe may be attached to Dam1p and an assay for binding by Fluorescence Resonance Energy Transfer (FRET) of the fluorescent probe on the microtubule may be conducted. Alternatively, binding may be assayed by fluorescence anisotropy. Another approach is to make Dam1p radioactive, attach microtubules to a solid matrix containing a scintilant, and use a scintillation proximity assay.

Figure 1B:
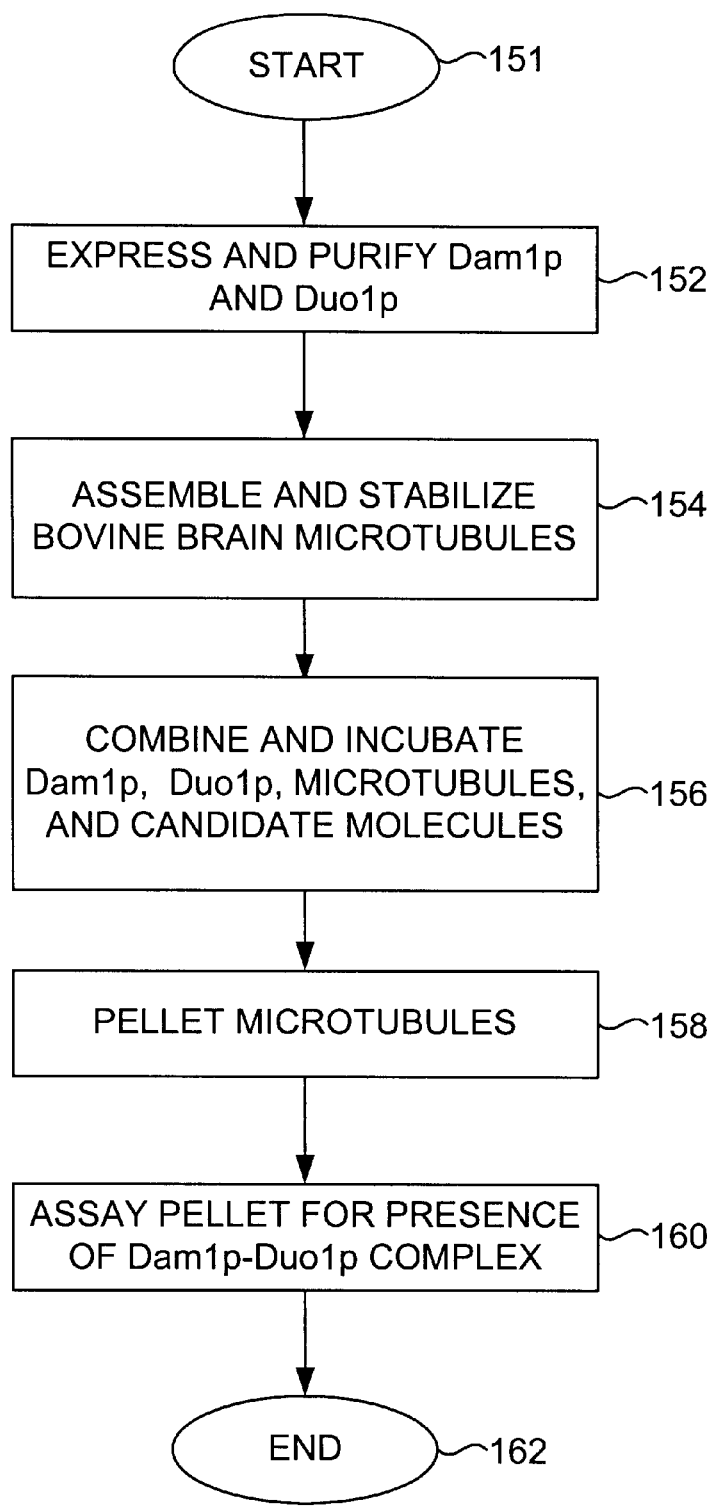

A preferred screening procedure using the Dam1p-Duo1p interaction is illustrated in the process flow of FIG. 1B. The process begins at 151, and at steps 152 and 154 Duo1p is produced and purified, preferably to 90% or greater purity, using a bacterial or yeast expression system, and bovine brain microtubules are assembled and stabilized, as described above. Several assays may be used. In one permutation, since Duo1p binds to Dam1p which in turn binds to microtubules, Dam1p and Duo1p are incubated with microtubules and small molecule drug development candidates at a step 156, as described above, only this time a fluorescent probe or radioactive moiety is attached to Duo1p. Dam1p-mediated interaction of Duo1p with microtubules is then assayed for as described above for Dam1p and microtubules. Briefly, at a step 158, microtubules are pelleted, and the pellet is then assayed for presence of the Duo1p-Dam1p complex at a step 160. Absence of Duo1p-Dam1p in the microtubule pellet indicates that the candidate small molecule inhibits the Dam1p-microtubule interaction and is a promising anti-mitotic agent development candidate. The process ends at 162.

In a second permutation, the Dam1p-Duo1p interaction may be directly assayed by immobilizing one of these two proteins on a solid matrix, labeling the other protein with a fluorescent or radioactive tag, and using a FRET or scintillation assay.

In a third permutation, the technology that first demonstrated the Duo1p-Dam1p interaction, the two-hybrid interaction, may be applied. Both genes (DUO1 and DAM1) are cloned in two-hybrid plasmids and show a robust interaction in living yeast cells. Both plasmids may be transformed into a yeast strain and the interaction scored by the production of β-galactosidase. Screening may then be conducted in living yeast cells for compounds that inhibit this interaction by identifying compounds that produce lower β-galactosidase levels.

Expression of the DUO1 or DAM1 genes may also be monitored by fusing the promoter sequences for these genes to reporter genes, such as the gene encoding Green Fluorescent Protein (GFP) or β-galactosidase. Inhibitors that block the expression of these genes but not other yeast genes may be screened by scoring for specific loss of expression of the reporter gene fused to the appropriate promoter sequence.

Further details regarding screening techniques appropriate for use in accordance with the present invention may be found in the review article Nolan, J. P. and Sklar, L. A., *The Emergence of flow cytometry for sensitive, real-time measurements of molecular interactions*. (1998) Nature Biotechnology 16, 633, and the references cited therein, which are incorporated by reference herein for all purposes. Of course, other effective screening methods may be used to identify candidates for drug development using proteins in accordance with the present invention.

EXAMPLE

The following example provides details concerning the identification and characterization of a gene coding for a mitotic spindle protein, DUO1, its corresponding protein Duo1p, and an associated protein, Dam1p, in accordance with the present invention. It should be understood the following is representative only, and that the invention is not necessarily limited by the details set forth in these examples.

MATERIALS AND METHODS

Strains and Media

The yeast strains used in this study are listed in Table 1 (FIG. 2). Media were prepared and standard genetic techniques were carried out according to Rose et al., 1990. YPD is yeast rich medium and SM is synthetic minimal medium which was supplemented with the appropriate nutrients. The carbon source was 2% glucose, 2% raffinose, or 2% galactose and 2% raffinose.

Plasmid Construction and Other DNA Manipulations

All DNA manipulations were carried out by standard methods (Maniatis et al., 1982). Restriction endonucleases and other enzymes were purchased from either New England Biolabs (Beverly, Mass.) or Boehringer Mannheim Corp. (Indianapolis, Ind.). Taq DNA Polymerase was obtained from Perkin-Elmer/Cetus (Norwalk, Conn.).

DNA sequencing was performed by the UC Berkeley Sequencing Facility (Berkeley, Calif.) through the use of an Applied Biosystems sequencing machine. Primers used for both PCR and sequencing were purchased from either the Berkeley Oligo Synthesis Facility (Berkeley, Calif.) or Operon (Alameda, Calif.).

Plasmid Isolation and Sequencing

Plasmids were recovered from strains grown on glucose minimal plates under conditions which selected for an auxotrophic marker carried on the desired plasmid. Strains were grown to saturation in 5 ml of glucose minimal medium, pelleted, and washed once with water. Plasmids were isolated from these cells using the Qiagen Plasmid Miniprep Kit (Santa Clara, Calif). Cell lysis was achieved by resuspending yeast in the cell lysis buffer provided with the kit, adding about 100 μl of glass beads and vortexing for 5 to 10 minutes. Following lysis, the steps in the Qiagen protocol were followed. The isolated plasmids were then transformed into *E. coli* and plasmid DNA was isolated using the Qiagen Plasmid Miniprep Kit. This DNA was used for sequencing and subcloning.

General Immunofluorescence and Immunoblot Procedures

Yeast cells were grown to early log phase in minimal or rich medium. For galactose induction, cells were grown to log phase in medium containing either raffinose or glucose. Cells grown on glucose were washed twice with water and then diluted into medium containing galactose/raffinose. Galactose was added directly to medium containing raffinose. Fixation and immunofluorescence procedures were carried out as described by Drubin et al. (1988). The YOL134 anti-tubulin antibody was used at 1:200 and the anti-Duo1p antibody (preparation described below) at 1:2000. Fluorescein-conjugated anti-heavy chain secondary antisera were obtained from Cappel/Organon Teknika (Malvern, Pa.).

Immunoblot analysis was performed using standard SDS-polyacrylamide and immunoblot transfer methods (Maniatis et al., 1982). The anti-Duo1p antibody was used at a dilution of 1:2000 for immunoblot analysis.

Deletion of DUO1

A DUO1 disruption plasmid was constructed in three steps. A 1.2 kb PCR fragment amplified from pDD465 (contains genomic DUO1 fragment) using M13Reverse and oCH18 (CCA TCG ATA TTG AAG ACT TGT TCA) (SEQ ID NO: 1) was digested with ClaI and XhoI and ligated into Bluescript SK+. A 0.7 kb NheI-HindIII fragment (HindIII site Klenowed) from pDD465 was then inserted into XbaI and EagI site of the above plasmid (EagI site Klenowed) resulting in vector pDD468. The HIS3 auxotrophic marker of plasmid LV1 was cloned into the BamHI site of pDD468 creating pDD469. URA3 was cloned from LV4 into the HinDIII site of pDD468 creating pDD470. A linear fragment was isolated from pDD469 or pDD470 after digestion with ClaI and SacI. This fragment was transformed into the diploid strain DDY1445 by the Li-acetate method. Colonies were selected for the integration of the HIS3 marker by plating on minimal medium. Gene disruption was confirmed by Southern analysis using the ECL Southern Analysis Kit (Amersham, Arlington Heights, Ill.).

Generation of Temperature-sensitive duo1 Mutants

The plasmid pDD467 (containing a genomic copy of DUO1 in pRS315) was mutagenized in vitro using hydroxylarnine (HA). Plasmid DNA (20 μg), carrying the selectable marker LEU2 and the DUO1 gene, was incubated at 75° C. in a solution containing the mutagen (0.5M Hydroxylamine hydrochloride, 50 mM sodium pyrophosphate, pH 7.0, 100 mM NaCl, 2 mM EDTA). Reactions were stopped by placing them on ice at the 0, 20, 40, 60, 80 and 100 minute time points. The mutagen was removed by spinning the reactions through two 1 ml G-25 syringe columns.

To determine the extent of mutagenesis, leuB⁻ bacteria were transformed with the mutagenized plasmids to monitor mutations in the LEU2 gene. The mutation rate was defined as the percentage of bacterial transformants that were unable to grow on M9-leucine medium. Plasmids from the 20 minute and 40 minute time points, that gave 8% and 11% LEU2 mutagenesis respectively, were used for further studies.

The mutagenized plasmids were transformed into a diploid strain that had both DUO1 loci deleted and carried a genomic copy of DUO1 on a URA3 marked CEN plasmid (pDD466). Transformants were plated on SC-Leu plates (plates containing all amino acids necessary for growth with the exception of leucine) at a density of about 300 colonies per plate. A total of 11,200 colonies were screened for the 20 minute time point, and 3,300 colonies were screened for the 40 minute time point. After 2 to 3 days of growth at 25° C., the colonies were replica plated onto 5-fluoroorotic acid (5-FOA) plates and incubated at 25° C. and 37° C. Strains containing a URA3 plasmid are not able to grow on medium containing 5-FOA. This step was carried out to select colonies that had lost the umnutagenized genomic copy of DUO1 marked with URA3 and only carried the mutagenized form marked with LEU2. Cells that did not grow at 37° C. but did grow at 25° C. on 5-FOA after three days were restreaked onto SC-Leu (synthetic complete medium lacking leucine) plates from the SC-Leu plates with the original transformants. These isolates were retested for growth on 5-FOA. The plasmids were recovered from all the 5-FOA selected clones and genomic inserts were cloned into an unmutagenized pRS315 vector as a ClaI-HinDIII fragment. These constructs were retested. The open reading frames of the temperature-sensitive isolates duo1-1 (pDD476) and duo1-2 (pDD477) were sequenced to identify the mutations.

Duo1p Antibody

The DUO1 coding sequence was amplified by PCR using primers oCH35 (GGA CTA GTG AGC AAA GCC AAT TAG ATG) (SEQ ID NO: 2) and oCH38 (GCG CGT CTA GAC CCG AAT CTT AAT TAT TTA CC) (SEQ ID NO: 3). The product was cloned into pHAT2 in frame with a six histidine tag (pDD471) using the SpeI site in oCH35 and the HinDIII site in oCH38. The construct was transformed into BL21 cells and expression of the fusion protein was induced by addition of 0.4 mM IPTG for 4 hrs at 37° C. Inclusion bodies were harvested from 6 liters of log phase cells and solubilized by the addition of 8 M urea. The denatured fusion protein was purified on a Qiagen NTA-column as described in the product protocol. The protein was refolded by stepwise dialysis from 8 M urea into PBS (137 mM NaCl, 2.7 mM KCl, 4.5 mM Na2HPO4 7H2O, 1.2 mM KH2PO4, pH 8.0) using a 2 M urea reduction per step.

Antibodies were generated by injecting rabbits with the purified protein. An affinity matrix was created by immobilizing the fusion protein on Reacti-gel resin (Pierce, Rockford, Ill.). The protein was attached to the resin as described in the manual. Sera was circulated over the column and specific antibodies were purified by MgCl2 elution (Harlow and Lane, 1988). The eluted antibody recognized the injected recombinant protein, a single 32 kD protein in whole yeast cell extracts and a GST-Duo1p fusion protein purified from yeast. Cells overexpressing Duo1p showed a clear increase in immunoreactivity in the 32 kD polypeptide in whole cell extracts, strongly supporting the conclusion that the 32 kD band was Duo1p.

Duo1p Immunofluorescence and Immuno Electron Microscopy

Yeast cells were grown to early log phase in either YPD or minimal medium. DUO1 overexpressing cells were grown in minimal medium containing raffinose to early log phase and induced for 6–18 hrs by the addition of galactose. Cells were processed for immunofluorescence microscopy as described previously (Pringle et al., 1991). For Duo1p staining, the cold methanol/acetone treatment was replaced by incubating cells with 0.1% SDS in PBS/BSA for 2 min. The monoclonal anti-a-tubulin antibody YOL134 was used at a 1:200 dilution, and the anti-DUO1 antibody was used at a 1:2000 dilution. Detection of the primary antibody was accomplished by applying fluorescein labeled anti-rat or anti-rabbit secondary antibodies (Cappel/Organon Teknika, Malvern, Pa.) at a dilution of 1:1000. Cy3 secondary anti-rabbit antibodies (Sigma, St. Louis, Mo.) were used at a 1:500 dilution.

Cells were cryofixed in a Bal-Tec HPM 010 high pressure freezer, freeze substituted in 0.2% glutaraldehyde plus 0.1% uranyl acetate in acetone for 2 days at −78° C., then warmed to −50° C. over a 12 hour period. Cells were infiltrated with Lowicryl HM20 at −50° C. and polymerized in BEEM capsules at −35° C. by UV irradiation. Blocks were UV irradiated at room temperature for an additional 48 hours to complete the resin curing. Thin (50 nm) sections were cut on a Reichert UltracutE microtome and picked up on Formvar and carbon coated nickel grids. The sections were incubated in primary antibody diluted 1:50 for 1 hour, rinsed with PBS, incubated in 10 nm goat anti-rabbit secondary diluted 1:20 for 1 hour, rinsed with PBS, fixed in 0.5% glutaraldehyde for 5 minutes, rinsed in dH20, and post-stained with uranyl acetate and lead citrate. Sections were examined in a JEOL 100CX electron microscope.

Purification of GST-Duo 1p from Yeast

The entire coding sequence of DUO1 was cloned into a galactose-inducible yeast GST fusion vector and tested for expression. A PCR product using primers oCH35 (GGA CTA GTG AGC AAA GCC AAT TAG ATG) (SEQ ID NO: 2) and oCH38 (GCG CGT CTA GAC CCG AAT CTT AAT TAT TTA CC) (SEQ ID NO: 3) was cloned into the pEG-KT vector resulting in pDD475. Transformants were grown in medium containing raffinose and expression was monitored after galactose induction. Expression reached a maximum level after 2 hours of induction. A total of 150 liters of cells were grown to log phase in raffinose, induced with galactose for 4 hours, and then harvested. Cells were washed once in ice cold water, frozen in liquid nitrogen, and then stored at −80° C. Cells were lysed in a Waring blender and resuspended in lysis buffer (50 mM Tris-Cl, pH 7.5, 1% Triton X-100, 150 mM NaCl, 2 mM MgCl2, 1 mM EDTA, 0.5 mM PMSF and aqueous protease inhibitors (0.5 $\mu$g/ml each of antipain, leupeptin, pepstatin A, chymostatin and aprotinin). The extract was spun at 10,000 g for 10 min. The supernatant was recovered, pre-swollen GST-beads were added, and the mixture was incubated at 4° C. for 4 to 14 hours. Beads were harvested by centrifugation at 1000 g for one minute, washed three times in wash buffer (50 mM Tris-Cl, pH 7.5, 1% Triton X-100, 300 mM NaCl, 2 mM MgCl2, 1 mM EDTA, 0.5 mM PMSF and 0.5 $\mu$g/ml aqueous protease inhibitors), and then washed with elution buffer. GST-Duo1p was eluted from beads by the addition of 15 mM glutathione in PME (80 mM Pipes, pH 6.8, 1 mM EGTA, 1 mM MgCl2) at room temperature for 30 to 60 minutes. Beads were collected by centrifugation at 1000 g for one minute. The supernatant containing the fusion protein was recovered, flash frozen, and stored at −80° C.

Microtubule Binding Experiments

Bovine tubulin at a concentration of 8 mg/ml in PME (80 mM Pipes, pH 6.8, 1 mM EGTA, 1 mM MgCl2) was thawed and prespun in a microfuge for 5 minutes at 4° C. GTP was added to a final concentration of 1 mM and tubulin was assembled into microtubules at 34° C. for 30 min. After assembly, taxol was added to a concentration of 20 $\mu$M and the microtubules were incubated for 15 minutes at room temperature. Microtubules were diluted in PME containing 1 mM GTP and 10 $\mu$M taxol.

For co-sedimentation experiments, in vitro translated protein using the TNT T7 Quick kit (Promega, Madison, Wis.)) was added to each 40 $\mu$l sedimentation reaction. The mixture was incubated for 20 minutes at room temperature to allow binding to occur. The mixture was then spun at room temperature in a TLA100 at 60,000 rpm for 10 minutes. Binding was evaluated by analyzing audioradiographs using an IS-1000 densitometer (Alpha Innotech Corporation, San Leandro, Calif.).

Two-hybrid Screen

A two-hybrid screen was carried out as described by Fields and Song (1989). Primers oCH36 (GCG CCC ATG GAG CAA AGC CAA TAA GAT GAT TCG) (SEQ ID NO: 4) and oCH37 (GCG GAT CCT AGA TAC ATT CCC G) (SEQ ID NO: 5) were used to PCR amplify DUO1 from a plasmid and the PCR product was cloned into the AS1-CHY2 DNA binding domain vector creating pDD473, which was used as a bait to find binding partners in a cDNA library fused to the GAL4 activation domain. Alter the initial screen using both HIS3 to select for activation, and LacZ expression as reporter of activation, the plasmids of all positive clones were recovered as described above. Over 800,000 transformants were screened using full length Duo1p as bait. A total of 174 positive clones remained positive after retesting. These clones were sequenced in batches of 40. Presence of plasmid inserts was confirmed by XhoI digestion before sequencing. Every clone that was identified at least twice by sequencing was used to probe all remaining unsequenced isolates by DNA hybridization using an Amersham ECL Southern Analysis Kit. This scheme allowed us to reduce the number of clones which required sequencing. For hybridization analysis, inserts were PCR-amplified directly from the plasmid recovered from yeast using the primers SY25 (GAG ATC TOG AAT TCG GAT CC) (SEQ ID NO: 6) and oCH41 (GGC ATG CCG GTA GAG GTG TGG) (SEQ ID NO: 7). Two microliters of each PCR reaction were spotted onto a 12 by 12 grid drawn onto nitrocellulose filters. Filters spotted with the PCR-amplified sequences were probed using the Amersham ECL Southern Analysis kit.

Subcloning of DAM1

The clones that were isolated in the two-hybrid screen were PCR-amplified from genomic DNA isolated from the yeast stain DDY 1102: DAM1 was amplified using primers oCH52 (GCG GGA TCC ATG AGC GAA GAT AAA GCT AAA TTA GGG) (SEQ ID NO: 8) and oCH56 (CTA GTC TAG AAT CAG TCA GCT CAT C) (SEQ ID NO: 9). All 5' primers contained the sequence for a BamHI restriction site and the original ATG of the individual clone. The 3' primers were located 100–200 bp downstream of the stop codon and contained a XbaI restriction site. The PCR products were subcloned into the Bluescript SK+ vector (pDD478) and into the galactose-inducible GFP (Green Fluorescent Protein) construct pDD113 (pDD480).

A DAM1 deletion construct was created by PCR using primers oCH46 (CTG ATA AGC TCA GCA ATT GCA CCA AAA CAA TAT GAG AAA AGG CTT GTA TTG CCA CTT TCA CCG ATT GTA CTG AGA GTG CAC C) (SEQ ID NO: 10) and oCH47 (TTG TGA GGA GGA TAA TTC TTT GGT TOG GTT GGG CGT AGT CAT CTG AAG GGG GGC CTT GTA CTG TGC GGT ATT TCA CAC CGC) (SEQ ID NO: 11) and vector pRS313 as a template. The construct was purified by agarose gel electrophoresis and transformed into DDY1102. Correct integration was tested by genomic PCR using primers oCH48 (GCG TTG CCC GGA CAA TAT CG) (SEQ ID NO: 12) and oCH49 (CTG CCT TCC TCC CTA TTG C) (SEQ ID NO: 13).

Localization and Overexpression of Dam1p

To localize Dam1p using the GFP-fusion constructs, the plasmids were transformed into strain DDY757 or DDY759. The strains were grown in minimal medium containing glucose into early log phase, washed in water and induced by resuspension in minimal medium containing 2% galactose/raffinose. After at least 6 hours of fusion protein overexpression at 30° C., GFP-fusion protein localization was observed directly by fluorescence microscopy.

Alternatively, cells were fixed, stained with the YOL134 anti-tubulin antibody, and examined by fluorescence microscopy. To determine whether Dam1p overexpression was lethal, its open reading frame was cloned behind the galactose promoter in pDD42 (pDD482 and then transformed into yeast strain DDY759. These yeast strains were streaked onto glucose and galactose plates and incubated at 30° C.

RESULTS

Duo1p Overexpression Causes Spindle Abnormalities

DUO1 (Death Upon Overproduction) (YGL061c) was isolated in a screen for genes which are toxic when overexpressed and cause morphlogical arrest phenotypes suggestive of defects in cytoskeleton function (Hofmann et al., in preparation). Cells overexpressing DUO1 arrested at the large-budded cell cycle stage. DAPI staining revealed that these cells arrested with a single undivided nucleus. This phenotype suggested a defect in mitotic spindle function because the mitotic checkpoint arrests yeast at the large-budded stage and because large budded yeast typically contain a divided nucleus Hoyt et al., 1990; Jacobs et al., 1988; Li et al., 1993; Reijo et al., 1994; Saunders and Hoyt, 1992). DUO1 was also identified in a screen in which overexpression of CLN2, a gene which encodes a G1 cyclin, could suppress the lethal phenotype of overexpressed genes. CLN2 overexpression suppressed the overexpression lethality of DUO1. The results presented below focus on the mitotic function of Duo1p.

Consistent with the arrest phenotype described above, cells overexpressing DUO1 contain abnormal microtubule arrangements. After 8 hours of DUO1 overexpression induced from a galactose-regulated promoter, 91% of yeast cells contained a short mitotic spindle. After 16 hours of overexpression, no microtubules were observed by immunofluorescence in 99% of arrested cells. This block with short mitotic spindles can be seen well when the spindle pole bodies are stained with Tub4p antibodies. The spindle pole bodies remain separated by only about the diameter of the nucleus. Since essentially all of the arrested cells contained two distinct spindle pole bodies, we conclude that spindle pole body duplication is unaffected by DUO1 overexpression. FACs analysis of haploid cells overexpressing Duo1p revealed an average DNA content of about 4N. Thus, the arrest caused by DUO1 overexpression appears not to have resulted from inhibition of DNA replication.

The DUO1 gene encodes a protein of 247 amino acid (MW=27.5 kD) having the following amino acid sequence:
1 MSEQSQLDDS TIDKLIPQIF NEMRSNLNNT TNKF-PKSTGG
41 GASDNISANS NSIRSFNSIT TQSLLKESES LDKITA-MIKN
81 VTAALKNNLP VYVNQVHEVC KSTNSILDSW INIHSQAGYI
121 HKLMSDQTYL KLINDRLHNE NVNTNDEDGS TLHNVIALKK
161 KEILDLRQKL ENRKGEKDAA PAKPPNQGLN PRYGVQSGRR
201 PVPSAGISNN GRVRKTHVPA SKRPSGIPRV TNR-WTKPTAS
241 SSRKMFR (SEQ ID NO: 14)

Analysis of the protein sequence failed to reveal similarity to other proteins in the public databases or structural motifs. The DUO1 gene and duo1p protein sequences are also available online from the Saccharomyces Genome Database at http://genome-www.stanford.edu/Saccharomyces, the disclosure of which is incorporated by reference herein.

Duo1p Co-localizes with Spindle Microtubules

A rabbit antibody was raised against bacterially expressed Duo1p containing a six His-tag. After affinity purification, the antibody recognized a single band at the predicted size for Duo1p (32 kD) in yeast whole cell extracts. Indirect immunofluorescence microscopy experiments using this antibody showed that the protein is located along nuclear microtubules and appears concentrated at spindle pole bodies. Duo1p does not appear to co-localize with cytoplasmic microtubules. Consistent with this observation, in G1, a cell cycle stage during which spindle assembly has not yet occurred, Duo1p staining is only seen in the vicinity of the spindle pole body. Localization of a GFP-Duo1p fusion protein yielded the same results.

The spindle localization of Duo1p was confirmed by immuno-electron microscopy. Staining of thin sections of yeast cells with Duo1p antibody and gold-labeled secondary antibodies showed co-localization with spindle microtubules, but not with cytoplasmic microtubules.

To determine whether the localization of Duo1p was dependent on microtubules in vivo, microtubules of wild-type strain DDY898 were depolymerized by the addition of 20 μg/ml benomyl. After incubation for two hours at 25° C., immunofluorescence revealed that essentially all of the microtubules were depolymerized. With the elimination of microtubules, Duo1p staining also vanished.

Temperature-sensitive duo1 Mutants Display a Spindle Elongation Defect

Deletion of DUO1 showed that the gene is essential. Therefore, to examine the loss-of-function phenotype of DUO1 in vivo, we created conditional-lethal alleles. A plasmid carrying the entire DUO1 open reading frame was mutagenized using hydroxylamine. Plasmids conferring temperature-sensitivity in a duo1 deletion strain were isolated. We recovered two temperature-sensitive alleles. Each allele carries two mutations. pDD476 has the mutations E67K and A157V and pDD477 has the mutations A117T and M124I. To examine the temperature-sensitive phenotype, strains carrying the mutated gene were grown at 25° C. and then shifted to 37° C. The morphologies of wild-type control cells and duo1 mutant cells were examined every 3 hours for 12 hours. Results are shown in Table 2, FIG. 3. During this time, cells were maintained in log phase. The cell cycle distribution of wild-type cells as evaluated by cell morphology was not affected dramatically by the temperature shift. The mutant cultures, on the other band, contained cells with short misaligned spindles, cells which appeared to have two unconnected half spindles and, after longer periods, cells which contained no microtubules at all. The primary defect seems to be the inability to elongate the spindle since this is the first of the defects to be observed. The duo1-2 allele appears more severe than duo1-1 since cells containing no microtubules appeared 18 hours after a shift to the non-permissive temperature for the former, and after about 24 hours for the latter.

Identification of a Protein, Dam1p, Which Interacts with Duo1p

To identify a protein which might function with Duo1p, a two-hybrid screen (Fields and Song, 1989) was carried out (see Materials and Methods). Thirteen genes were recovered at least four times (DAM1, LCP5, PUP1, AIP2, CIM5, VMA8, DEP1, YIR004w, YMR012w, YER049w, YDR016c, YGR120c, YJL036w). Proteins encoded by genes of unknown function (DAM1, LCP5, CIM5, YIR004w, YMR012w, YER049w, YDR016c, YGR120c), and therefore with the possibility of possessing a function related to Duo1p, were localized as GFP-fusions. A protein showing spindle localization was characterized further (see below).

The gene for this protein was designated DAM1 (Duo1p And Mps1p interacting) (YER113w). The DAM1 gene and dam1p protein sequences are available online from the Saccharomyces Genome Database at http://genome-www.stanford.edu/Saccharomyces, the disclosure of which is incorporated by reference herein.

Precise genomic deletions of DAM1 showed that the gene is essential for viability. Dam1p is a protein of 335 aa (MW=37.8 kD) having the following amino acid sequence:

1   MSEDKAKLGT TRSATEYRLS IGSAPTSRRS SMGESSSLMK
41  FADQEGLTSS VGEYNENTIQ QLLLPKIREL SDSIITLDSN
81  FTRLNFIHES LADLNESLGS LLYGIMSNSW CVEFSQAPHD
121 IQDDLIAIKQ LKSLEDEKNN LVMEISNMER GIKRKKDEQG
161 ENDLAKASQN KQFNQPLFPS SQVRKYRSYD NRDKRKPSKI
201 GNNLQVENEE DYEDDTSSEA SFVLNPTNIG MSKSSQGHVT
241 KTTRLNNNTN SKLRRKSILH TIRNSIASGA DLPIENDNVV
281 NLGDLHPNNR IYSEWLQEW SMGPLRRTEI QCSQDVLKGN
321 PQKADILLQR KLKKK (SEQ ID NO: 15)

Database searches and sequence analysis did not identify any homologues in the public databases or sequence motifs.

To confirm that the two-hybrid interaction between Duo1p and Dam1p was the result of direct physical binding, in vitro translated Dam1p was incubated with glutathione beads coated with GST or GST-Duo1p. The beads were pelleted, washed with buffer containing 50 mM NaCl, and the presence of the in vitro translated products in the supernatant and pellet fractions was monitored by analysis on protein gels. Dam1p interacts strongly with GST-Duo1p but not with GST alone. An in vitro translated fragment of mammalian tau protein (see below) served as a negative control, and did not interact with either GST or GST-Duo1p coated beads.

To determine the intracellular localization of Dam1p, GFP fusion plasmids were constructed. GFP-Dam1p was found exclusively associated with the intranuclear spindle throughout the cell cycle. Overexpression of Damp1 is toxic (see below). In addition, overexpression of wild-type Dam1p and GFP-Dam1p had the exact same effect on cell growth, indicating some degree of functionality for the GFP-fusion protein.

Dam1p Binds to Microtubules

Attempts to demonstrate direct interaction of Duo1p with microtubules gave ambiguous results. GST-Duo1p purified from yeast (see Materials and Methods) co-sedimented partially with yeast and bovine microtubules. Only a about 9% of the protein bound to microtubules and an increase in microtubule concentration did not result in increased Duo1p pelleting. Furthermore, binding did not appear fully reversible. Dilution after binding did not reduce the amount of pelletable Duo1p, and even washes with 1 M NaCl resleased only half of the bound GST-Duo1p, raising concerns over whether this interaction was physiologically relevant, or resulted from trapping of GST-Duo1p on the microtubules. Thus, these studies, while consistent with a direct Duo1p-microtubule interaction, failed to demonstrate such an interaction uneqivocally. Therefore, the question of what interaction might account for co-localization of Duo1p with spindle microtubules remained open.

The binding of Dam1p to microtubules was then tested. It was found that Dam1p co-sediments with bovine microtubules in a concentration-dependent manner. In co-sedimentation experiments at a microtubule concentration of 5 $\mu$M, approximately half of Dam1p was found in the pellet and half in the supernatant, indicating that the KD of the interaction is approximately 5 $\mu$M. Furthermore, when binding reactions were diluted 10 fold after binding reached equilibrium, the amount of in vitro translated Dam1p found in the pellet was markedly reduced. These observations show that Dam1p binds microtubules specifically and reversibly.

Dam1p Overexpression is Lethal and Causes Spindle Defects

The overexpression phenotype for DAM1 was determined. Overexpression of the wild-type gene gave the same phenotype as overexpression of the GFP-fusion. Overexpression of Dam1p was lethal, resulting in a large budded cell cycle arrest in about 90% of the cells. The nuclei in these cells were undivided and the microtubules were abnormal. Approximately 20% of the cells had short spindles, with the rest of the cells having no microtubule structures or only a small spot that was detected by tubulin antibodies. After ten hours of DAM1 overexpression, no microtubules were detected by immunofluorescence. This phenotype is reminiscent of that caused by Duo1p overproduction. However, in contrast to the DUO1 overexpression lethality, lethality due to DAM1 overexpression is not suppressed by CLN2 overexpression.

References

The following documents, cited above, are incorporated by reference herein for all purposes:

Berlin, V., Styles, C. A., and Fink, G. R. (1990): BIK1, a protein required for microtubule function during mating and mitosis in *Saccharomyces cerevisiae*, colocalizes with tubulin. *J. Cell Biol* 111, 2573–86.

Cottingham, F. R., and Hoyt, M. A. (1997): Mitotic spindle positioning in *Saccharomyces cerevisiae* is accomplished by antagonistically acting microtubule motor proteins [see comments]. *J. Cell Biol* 138, 1041–53.

Drubin, D. G., Miller, K. G., and Botstein, D. (1988): Yeast actin-binding proteins: Evidence for a role in morphogenesis. *J. Cell Biol.* 107, 2551–2561.

Fields, S., and Song, O. (1989): A novel genetic system to detect protein-protein interactions. *Nature* 340, 245–6.

Gambino, J., Bergen, L. G., and Morris, N. R. (1984): Effects of mitotic and tubulin mutations on microtubule architecture in actively growing protoplasts of Aspergillus nidulans. *J. Cell Biol.* 99, 830–838.

Hardwick, K. G. (1998): The spindle checkpoint. TIGS 14, 1–4.

Harlow, E., and Lane, D. (1988)Antibodies-a laboratory manual, Cold Spring Harbor Laboratory, Cold Spring Harbor.

Hoyt, M. A., Stearns, T., and Botstein, D. (1990): Chromosome instability mutants of *Saccharomyces cerevisiae* that are defective in microtubule-mediated processes. *Mol. Cel. Biol.* 10, 223–34.

Jacobs, C. W., Adams, A. E., Szaniszlo, P. J., and Pringle, J. R. (1988): Functions of microtubules in the *Saccharomyces cerevisiae* cell cycle. *J. Cell Biol* 107, 1409–26.

Li, R., Havel, C., Watson, J. A., and Murray. A. W. (1993): The mitotic feedback control gene MAD2 encodes the alpha-subunit of a prenyltransferase [published erratum appears in Nature 1994 Sep 29;371(6496):438]. *Nature* 366, 82–4.

Machin, N. A., Lee, J. M., and Barnes, G. (1995): Microtubule stability in budding yeast: characterization and dosage suppression of a benomyl-dependent tubulin mutant. *Mol. Biol. Cell* 6, 1241–59.

Maniatis, T., Fritsch, E. F., and Sambrook., J. (1982): *Molecular cloning: a laboratory manual*. Cold Spring Harbor Laboratory. Cold Spring Harbor, N.Y.

Marschall, L. G., Jeng, R. L., Mulholland, J., and Steams, T. (1996): Analysis of Tub4p, a yeast gamma-tubulin-like protein: implications for microtubule-organizing center function. *J. Cell Biol* 134, 443–54.

Masuda, H., and Cande, W. Z. (1987): The role of tubulin polymerization during spindle elongation in vitro. *Cell* 49, 193–202.

Nicklas, R. B. (1997): How cells get the right chromosomes. *Science* 275, 632–7.

Oakley, B., and Morris, N. R. (1980): Nuclear movement is b-tubulin dependent in *Aspergillus nidulans. Cell* 19, 255–262.

Oakley, B. R. (1994): *Gamma-tubulin*. Wiley-Liss, Inc., New York. N.Y.

Oakley, B. R., and Rinehart, J. E. (1985): Mitochondria and nuclei move by different mechanisms in *Aspergillus nidulans. J. Cell Biol.* 101, 2392–2397.

Pasqualone, D., and Huffaker, T. C. (1994): STU1, a suppressor of a beta-tubulin mutation, encodes a novel and essential component of the yeast mitotic spindle. *J. Cell Biol* 127, 1973–84.

Pellman, D., Bagget, M., Tu, Y. H., Fink, G. R., and Tu, H. (1995): Two microtubule-associated proteins required for anaphase spindle movement in *Saccharomyces cerevisiae* [published erratum appears in J Cell Biol 1995 Oct;131 (2):561]. *J. Cell Biol.* 130, 1373–85.

Pringle, J. R., Adams, A. E., Drubin, D. G., and Haarer, B. K. (1991): Immunofluorescence methods for yeast. *Meth. Enzymol.* 194, 565–602.

Reijo, R. A., Cooper, E. M., Beagle, G. J., and Huffaker, T. C. (1994): Systematic mutational analysis of the yeast beta-tubulin gene. *Mol. Biol. Cell* 5, 29–43.

Roof, D. M., Meluh, P. B., and Rose, M. D. (1992): Kinesin-related proteins required for assembly of the mitotic spindle. *J. Cell Biol.* 118, 95–108.

Rose, M. D., Winston, F., and Hieter, P. (1990): *Methods in Yeast Genetics*. Cold Spring Harbor Laboratory Press. Cold Spring Harbor, New York.

Rout, M. P., and Kilmartin, J. V. (1990): Components of the yeast spindle and spindle pole body. *J. Cell Biol* 111, 1913–27.

Rudner, A. D., and Murray, A. W. (1996): The spindle assembly checkpoint. *Current Opinion in Cell Biology* 8, 773–80.

Saunders, W. S., and Hoyt, M. A. (1992): Kinesin-related proteins required for structural integrity of the mitotic spindle. *Cell* 70, 451–8.

Sobel, S. G. (1997): Mini review: mitosis and the spindle pole body in *Saccharomyces cerevisiae. J. Exp. Zool.* 277, 120–38.

Sobel, S. G., and Snyder, M. (1995): A highly divergent gamma-tubulin gene is essential for cell growth and proper microtubule organization in *Saccharomyces cerevisiae. J. Cell Biol* 131, 1775–88.

Spang, A., Courtney, I., Grein, K., Matzner, M., and Schiebel, E. (1995): The Cdc31p-binding protein Kar1p is a component of the half bridge of the yeast spindle pole body. *J. Cell Biol* 128, 863–77.

Vallen, E. A., Ho, W., Winey, M., and Rose, M. D. (1994): Genetic interactions between CDC31 and KAR1i, two genes required for duplication of the microtubule organizing center in *Saccharomyces cerevisiae. Genetics* 137, 407–22.

Wang, P. J., and Huffaker, T. (1997): Stu2p: A Microtubule-binding protein that is an essential component of the yeast spindle pole body. *J. Cell Biol* 139, 1271–1280.

Waters, J. C., and Salmon, E. (1997): Pathways of spindle assembly. *Current Opinion in Cell Biology* 9, 3743.

Winey, M., Mamay, C. L., O'Toole, E. T., Mastronarde, D. N., Giddings, T. H., Jr., McDonald, K. L., and McIntosh, J. R. (1995): Three-dimensional ultrastructural analysis of the *Saccharomyces cerevisiae* mitotic spindle. *J. Cell Biol* 129, 1601–15.

Winsor, B., and Schiebel, E. (1997): Review: an overview of the *Saccharomyces cerevisiae* microtubule and microfilament cytoskeleton. *Yeast* 13, 399–434.

CONCLUSION

Two mitotic spindle proteins, Duo1p and Dam1p have been described. Both proteins are essential for viability. Neither showed informative sequence homologies.

Duo1p appears to associate exclusively with intranuclear microtubules and spindle pole bodies, but not with cytoplasmic microtubules. Two-hybrid and biochemical data showed that Duo1p interacts with the protein Dam1p. This interaction appears to be physiologically relevant since Dam1p is associated with intranuclear mitotic spindle microtubules. Furthermore, overproduction of Dam1p, like overproduction of Duo1p, causes mitotic defects. Co-sedimentation assays demonstrated specific binding of Dam1p to microtubules. The localization data for both proteins suggest that Duo1p may interact with Dam1p along intranuclear spindle microtubules. Since Dam1p binds to Duo1p and to microtubules, it is believed that it mediates interaction of Duo1p with microtubules.

Both Duo1p and Dam1p have been linked functionally to the mitotic spindle. Both DUO1 overexpression and DUO1 loss of function caused spindle defects and a large-budded arrest phenotype. The identification of the essential gene DAM1, whose protein products interacts with Duo1p may explain the observation that the loss of function and overexpression phenotypes of Duo1p are similar. It is believed that DUO1 overexpression mimics deletion of DAM1 by titration of one or both of their gene products.

The DUO1 loss of function and overexpression phenotypes suggest an essential role in spindle elongation. SPBs were separated in both cells overexpressing DUO1, and in duo1 loss of function mutants. SPB separation is microtubule dependent. While short spindles formed, they did not elongate. Therefore, Duo1p is critical for spindle elongation but does not seem to be involved in the initial step of spindle assembly.

These proteins are promising candidates for anti-mitotic agent development. Application of these proteins to the development of anti-fungal agents for use as pesticides on agricultural crops and for pharmaceutical applications may be particularly useful, since the lack of homology between these proteins and human proteins suggests that anti-mitotic agents effective against these fungal proteins would not have anti-mitotic activity against human cells thereby preventing any adverse health effects for humans contacting these agents.

Although the foregoing invention has been described in some detail for purposes of clarity of understanding, it will be apparent that certain changes and modifications may be practiced within the scope of the invention. It should be noted that there are may alternative ways of implementing both the processes and compositions of the present invention. Accordingly, the present embodiments are to be considered as illustrative and not restrictive, and the invention is not to be limited to the details given herein, but may be modified within the scope and equivalents of the appended claims.

What is claimed is:

1. A method for screening potential anti-mitotic agents comprising:
   a) providing one or more purified proteins that are required for yeast mitotic spindle formation, wherein the one or more proteins are selected from the group consisting of a protein encoded by the yeast gene YGR113w (Dam I), and proteins provided in a complex of the Duo 1 protein encoded by the yeast gene YGL061 c and the Dam I protein encoded by the yeast gene YGR113w,
   b) combining in vitro said one or more proteins with microtubules, and a potential anti-mitotic agent;
   c) incubating said one or more proteins, said microtubules, and said anti-mitotic agent;
   d) assaying the microtubules for binding of said one or more proteins; and
   e) identifying an anti-mitotic agent, wherein said anti-mitotic agent inhibits binding of said one or more proteins to said microtubules.

2. The method according to claim 1, wherein said microtubules comprise bovine brain microtubules.

3. The method according to claim 1, wherein said microtubules comprise mammalian microtubules.

4. The method according to claim 1, wherein said assaying comprises pelleting said microtubules by ultracentrifugation followed by polyacrylamide gel electrophoresis of the pellets to assess the inhibition of binding of said one or more proteins to said microtubules.

5. The method according to claim 1, wherein said assaying comprises attaching a fluorescent probe to at least one of said one or more proteins and assessing the inhibition of binding of said one or more proteins to said microtubules by measuring the amount of said fluorescent probe on said microtubules.

6. The method according to claim 5, wherein measuring comprises Fluorescent Resonance Energy Transfer (FRET) or fluorescence anisotropy.

7. The method according to claim 1, wherein said one or more proteins required for mitotic spindle formation consists of the Dam1p protein encoded by the yeast gene YGR113w.

8. The method according to claim 1, wherein said one or more proteins required for mitotic spindle formation are provided in a complex of the Duo1 protein encoded by the yeast gene YGL161c and the Dam1p protein encoded by the yeast gene YGR113w.

9. The method according to claim 8, wherein the assay for binding is an assay for assessing the binding of said complex to said microtubules.

* * * * *